(12) United States Patent
Fein et al.

(10) Patent No.: US 9,095,274 B2
(45) Date of Patent: Aug. 4, 2015

(54) REAL TIME MEDICAL DATA ANALYSIS SYSTEM

(75) Inventors: Gene Fein, Malibu, CA (US); Edward Merritt, Lenox, MA (US)

(73) Assignee: Empire Technology Development LLC, Wilmington, DE (US)

( * ) Notice: Subject to any disclaimer, the term of this patent is extended or adjusted under 35 U.S.C. 154(b) by 1563 days.

(21) Appl. No.: 12/202,282

(22) Filed: Aug. 31, 2008

(65) Prior Publication Data

US 2010/0056877 A1    Mar. 4, 2010

(51) Int. Cl.
| | |
|---|---|
| A61B 5/00 | (2006.01) |
| A61B 8/06 | (2006.01) |
| A61B 8/08 | (2006.01) |
| G06Q 50/22 | (2012.01) |
| A61B 8/00 | (2006.01) |
| A61B 5/0402 | (2006.01) |

(52) U.S. Cl.
CPC ............. *A61B 8/06* (2013.01); *A61B 8/0858* (2013.01); *A61B 8/565* (2013.01); *G06Q 50/22* (2013.01); *A61B 5/0402* (2013.01)

(58) Field of Classification Search
CPC ....... G06F 9/5402; G06Q 50/22; G06Q 50/24
See application file for complete search history.

(56) References Cited

U.S. PATENT DOCUMENTS

| | | | |
|---|---|---|---|
| 7,370,335 B1 * | 5/2008 | White et al. ................... | 719/328 |
| 7,539,994 B2 * | 5/2009 | McAlinden et al. .......... | 718/104 |
| 7,739,692 B2 * | 6/2010 | Fahy .............................. | 719/327 |
| 2004/0039259 A1 * | 2/2004 | Krause et al. ................. | 600/300 |
| 2005/0166239 A1 * | 7/2005 | Uchikubo et al. ............... | 725/78 |
| 2005/0246722 A1 * | 11/2005 | Shier et al. ..................... | 719/321 |
| 2006/0122864 A1 * | 6/2006 | Gottesman et al. ............... | 705/2 |
| 2007/0016914 A1 * | 1/2007 | Yeap .............................. | 719/328 |

* cited by examiner

*Primary Examiner* — Gary Jackson
*Assistant Examiner* — Shirley Jian
(74) *Attorney, Agent, or Firm* — Turk IP Law, LLC (57) ABSTRACT

A medical data analysis system utilizing a cloud computing resource. Exemplary embodiments provide real time medical testing data to a cloud computing resource via middleware. Exemplary middleware may condition the data for use by the cloud computing resource and the middleware may appropriately format the results of the analysis provided by the cloud for display on a user interface device.

46 Claims, 8 Drawing Sheets

REAL TIME MEDICAL DATA ANALYSIS SYSTEM

BACKGROUND

The present disclosure relates to medical data analysis systems. In particular, to system's that utilize a cloud computing resource to analyze medical data.

It is known that monitoring blood flow through blood vessels, organs, capillaries, and the entire vascular system may be helpful in diagnosing a patient's overall health. Blood flow measurements may be especially advantageous when a health care provider is diagnosing or screening for various cardiovascular conditions, aneurism risk, hypertension, clotting, or benign or malignant masses. Currently, the screening process for vascular issues can include physical examination, genetic screening, hereditary trait evaluation, magnetic resonance imaging (MRI) with or without contrast, hypertension readings, investigative scoping or biopsy procedure's, computed axial tomography (CAT or CT scan), or positron emission tomography (PET), as well as X-ray and ultrasound imaging.

BRIEF SUMMARY

Embodiments provide medical data analysis systems utilizing a cloud computing resource. Exemplary embodiments may provide real time medical testing data to a cloud computing resource via middleware. Exemplary middleware may condition the data for use by the cloud computing resource and the middleware may appropriately format the results of the analysis provided by the cloud for display on a user device, for example.

In one aspect, a method of analyzing medical data may include sensing at least one medical parameter of a patient to provide sensed medical data; transmitting the sensed medical data to a cloud computing resource for processing in at least near real time; receiving analysis results from the cloud computing resource; and transmitting the analysis results to a user interface device.

In another aspect, a method of analyzing medical data may include providing a middleware computing device including middleware, the middleware computing device being operatively coupled to at least one medical gathering device configured to gather medical data about a patient, and operatively coupled to a cloud computing device including an application adapted to analyze medical data and generate an analysis result; receiving, by the middleware computing device, the medical data about a patient from the medical data gathering device; transferring the medical data from the middleware computing device to the cloud computing resource; receiving an analysis result from the cloud computing resource by the middleware computing device; and transferring the analysis result to a user interface device.

In another aspect, a medical data processing system may include a middleware computing device including middleware, the middleware computing device adapted to receive sensed medical data from a medical data sensing device, and the middleware computing device being operatively coupled to a cloud computing resource having at least one application for processing the sensed medial data and being operatively couple to a user interface device.

The Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, computer programs and systems related to the analysis of medical data utilizing a cloud computing resource.

Exemplary embodiments of the present disclosure may provide a medical data analysis system offering improved efficiency for complex medical testing by utilizing a cloud computing infrastructure to conduct complex matching, data analysis, and computations to generate useful testing results. Conventional models of screening for vascular issues are well established. Even with nuclear magnetic resonance imaging (MRI) and other non-invasive methods, the only way for a treating physician to definitively diagnose a particular condition with a high degree of certainty in many cases is to perform an invasive procedure. Unfortunately, many invasive procedures present an elevated risk to the patient as well as an increased expense over non-invasive testing. If an accurate topical or other sort of non-invasive test could provide additional data to the health care providers charged with diagnosing the patient, then perhaps this would avoid the necessity of invasive procedures in some, or many cases.

Additionally, conventional systems often lack adequate baseline and historical guidelines for normal conditions, based upon archived data from the same non-invasive testing method on the same patient or other patients with similar demographics. Exemplary embodiments of the present disclosure may allow a patient's prior medical data to be coordinated via cloud computing resources for data analysis with new non-invasive test results to quickly yield a probability factor in testing for vascular irregularities, for example.

Exemplary embodiments of the present disclosure may provide an integrated system for testing of internal vascular issues as well as other medical tests dependent on real time data flow. Many of these tests may also be conducted using a non-invasive testing method that may provide additional data to the health care providers charged with diagnosing a patient. Such a testing system may avoid the necessity of invasive procedures in some or many cases. Additionally, the system may store and make available baseline and historical guideline data for normal conditions, based upon archived data from the same non-invasive testing style on the same patient or other patients with similar demographics. Data may be correlated using cloud computing resources for data analysis with new test results to quickly produce results of the testing for vascular irregularities, for example. This data provided by the cloud computing infrastructure may be quickly configured by a middleware solution and securely transmitted to health care providers to enable the patient to obtain prompt testing results.

Exemplary embodiments of the present disclosure include a system that may be adapted for medical testing and that acts upon real-time data. Such a system may be advantageous over medical testing that is based upon a post-measurement analysis of static data. Data that is collected by real-time testing, such as electrocardiograms, vascular flow readings, topical sensor readings, etc. may be utilized by an exemplary system to yield quick results with analytical data to not only assess the test results at hand, but also to analyze results against the patient's own history. Many of the medical applications benefiting from this embodiment may utilize dozens, hundreds, or more medical data inputs (sensor data and other medical readings), all of which are processed in real time or near real time by cloud computing.

In addition, exemplary embodiments may provide a demographic analysis involving the patient's test data compared to data obtained from other patients with the same or similar demographics. The comparison data may include data that was determined to be negative, positive and/or inconclusive for the same test. This analysis may be performed for a single test or can generate progressive analysis of multiple tests conducted on the patient over time. The system may assess archived conditions and current conditions to make a predictive diagnosis, thus enabling a health care provider to take the necessary steps in the patient's care as a result of the testing.

Exemplary embodiments of the present disclosure may be used to perform real time analysis on vascular testing data, for example. Vascular testing may be accomplished using sensors (such as internal gate sensors) floating through the bloodstream tracked by imaging technology, an ultrasonic device, and/or focused audio data readings, for example. In such an application, the speed at which the data can reach the cloud and be processed back through the middleware to the user may be an important factor. High speed transfer and processing of data may enable enhanced access to diagnostic data for the health care provider(s).

Figure 1:
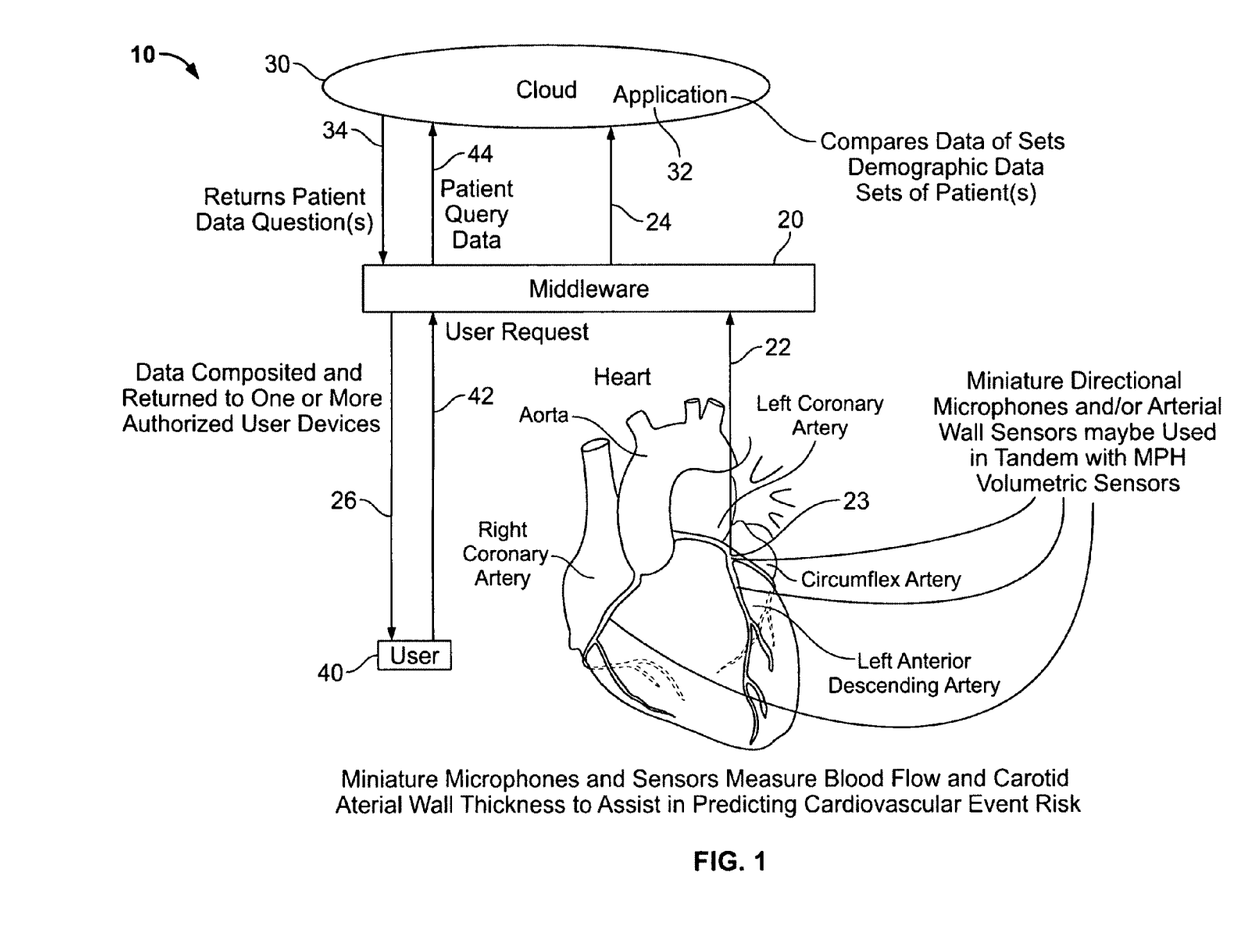
FIG. 1 is a schematic diagram of an exemplary embodiment for vascular flow data analysis.

In an exemplary embodiment shown in FIG. 1, sensors 23 (such as miniature microphones) may be used to measure blood flow and coronary artery wall thickness, for example. As is known in the art, various ultrasound technologies are capable of measuring many medical parameters. Certain ultrasound devices, for example, may be used to ascertain artery wall thicknesses, such as coronary artery wall thickness. Further, measurement, such as by an ultra sound device, of carotid and femoral artery wall thicknesses may be useful in predicting the risk of a cardiovascular event. Regarding blood flow measurement, Doppler ultrasound devices, for example, enable calculation of the flow rate of blood within blood vessels.

Figure 5:
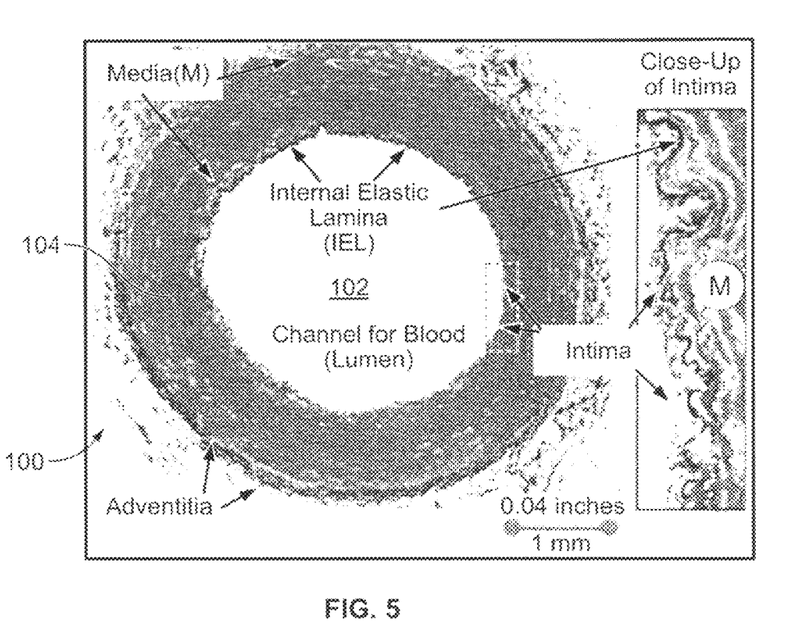
FIG. 5 is a cross section of a coronary artery.

The sensors 23 may provide real time data 22 that may be securely transferred to the middleware 20 of the system 10, which may be resident on one or more servers. The middleware 20 may reformat or package the data 22 for use by the cloud computing resource 30. The middleware 20 may then transfer the properly formatted data 24 to the cloud computing infrastructure 30. The cloud computing resource 30 may slot the data 24 into the appropriate place in a database for the patient, and, in some cases, into anonymous, demographic, and sortable categories enabling a database keyed analysis of user queried data. FIG. 5 depicts a cross section of a coronary artery 100 including the lumen 102 and the artery wall 104. Exemplary embodiments of the disclosure may also be used to measure carotid artery wall thickness.

In an exemplary embodiment involving an electrocardiogram (EKG), the patient's real-time EKG data 22 (which may be obtained using electrodes operatively connected to a medical data gathering device) may be securely forwarded to the middleware 20. The middleware 20 may condition the data 22 for the cloud computing resource 30. Such conditioning may include configuring or translating data 22, queries 42, or results 34 to be compatible with a specific file type, database, application, format and/or specification. A query 42 from a user interface device 40 (which may be operated by or at the direction of the patient's healthcare test provider or physician) may query the system 10. The query 42 (which may originate from one of many types of user devices, operating systems, and software application versions) may be received and processed by the middleware 20 for transmission to the cloud computing resource 30 in an appropriate format for the cloud computing resource's 30 operating system(s), application versions, device specifications, etc. as patient query data 44.

The exemplary cloud computing resource 30 may set the user query 44 within an application 32 to run an analysis of the data 24 in real time or in near real time. For example, the cloud computing resource 30 may compare the patient's medical data 24 with baseline medical data, the patients own history, and demographic data, all of which may be stored in or accessible by the cloud computing resource 30. The analysis may also include the generation of one or more reports by the cloud computing resource 30, which may include chronological graphical reports, including charts indicating healthy and unhealthy results in clear and easy to read display formats, for example. In an exemplary embodiment, the results 34 transmitted back to the middleware 20 may be specifically responsive to the user's query 42. An exemplary system may have the capability to analyze and distribute information in many diverse formats. Further, exemplary systems may utilize the robust computational power of the cloud to process data very quickly.

In an exemplary embodiment, once the results 34 have been received by the middleware 20 from the cloud, the middleware 20 may condition the results 34 so that the end user(s) authorized to receive the data result 26 of the query 42 can receive the data result 26 in a form that will be most conducive to viewing by the user based on the particular parameters of the users' interface device(s) 40. Such conditioning may include configuring or translating data 22, queries 42, or results 34 to be compatible with a specific file type, database, application, format and/or specification. For example, the results 26 may be formatted for display on the type of device (e.g., desktop computer, mobile or handheld device, etc.) utilized by the user. Utilizing the middleware 20 to manipulate data sent to and from end users' devices 40 may require programming for compatibility with each type of device, application programming interface (API), and/or operating system to ultimately deliver an application version that enables the information to be functional, accurate, and useful.

Data analysis in near real time or real time with the actual test readings may lead to the test being extended, refocused, or discontinued based upon the data analysis results. The same process may be used during surgical procedures where real time data monitoring may be utilized to generate predictive warnings and verify courses of treatment and choices made during the procedure. The ability to access extensive data from medical testing and procedures can provide doctors and other health care providers with a much larger, more easily accessible, and more detailed field of information from which to make more informed decisions about a patient's care immediately or over time.

Figure 2:
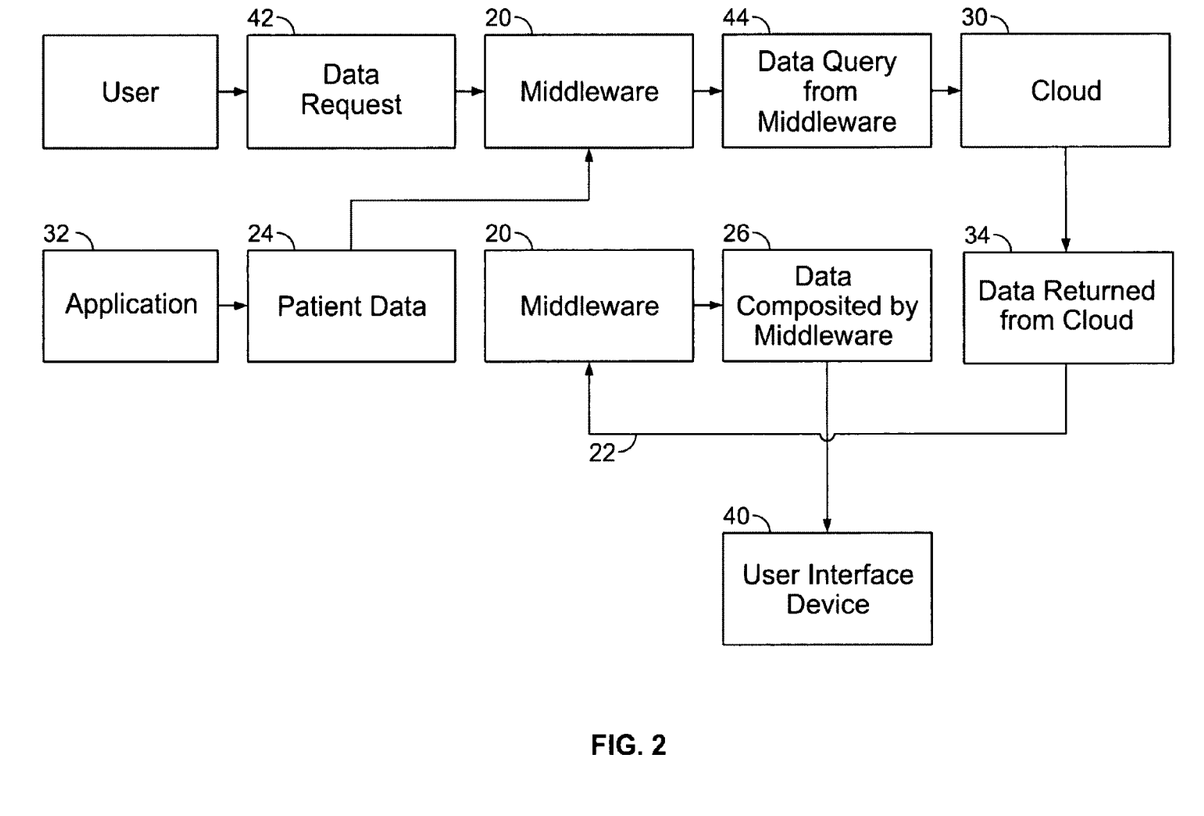
FIG. 2 is a flow chart depicting an exemplary embodiment for vascular flow data analysis.

As shown in FIG. 2, in an exemplary embodiment a user may initiate a data request 42 using a user interface device 40, which may bee transmitted to the middleware 20. The middleware 20 may send a query 44 to the cloud. The cloud 30 may provide data results 34 to the middleware 20, which may receive and adapt the results into results 26 for transmission to the user interface device 40. In addition, one or more applications 32 of the cloud computing resource 30 may operate on patient data 24 provided by the middleware 20.

In some exemplary embodiments, the user may utilize a portable user interface device 40 (such as a notebook or handheld computer) and the medical data sensor 23 may also be portable. The sensor 23 and the user interface device 40 (which may be integrated into a common unit) may be connectable to the middleware 20 from a plurality of locations, thus allowing the system to function in a mobile work environment.

In some embodiments, the cloud computing resource 30 may include or access medical data from a plurality of patients. In exemplary embodiments, because the medical data is stored within, or accessible by, the cloud and the applications are run within the cloud, a plurality of users may have access to the same data and applications via the middleware. Further, if the data and/or applications are updated, all users may immediately have access to the updated data and/or applications. This is in contrast to conventional systems relying on local data analysis and storage, which may require updates to applications and data to be installed locally on each user device.

Figure 3:
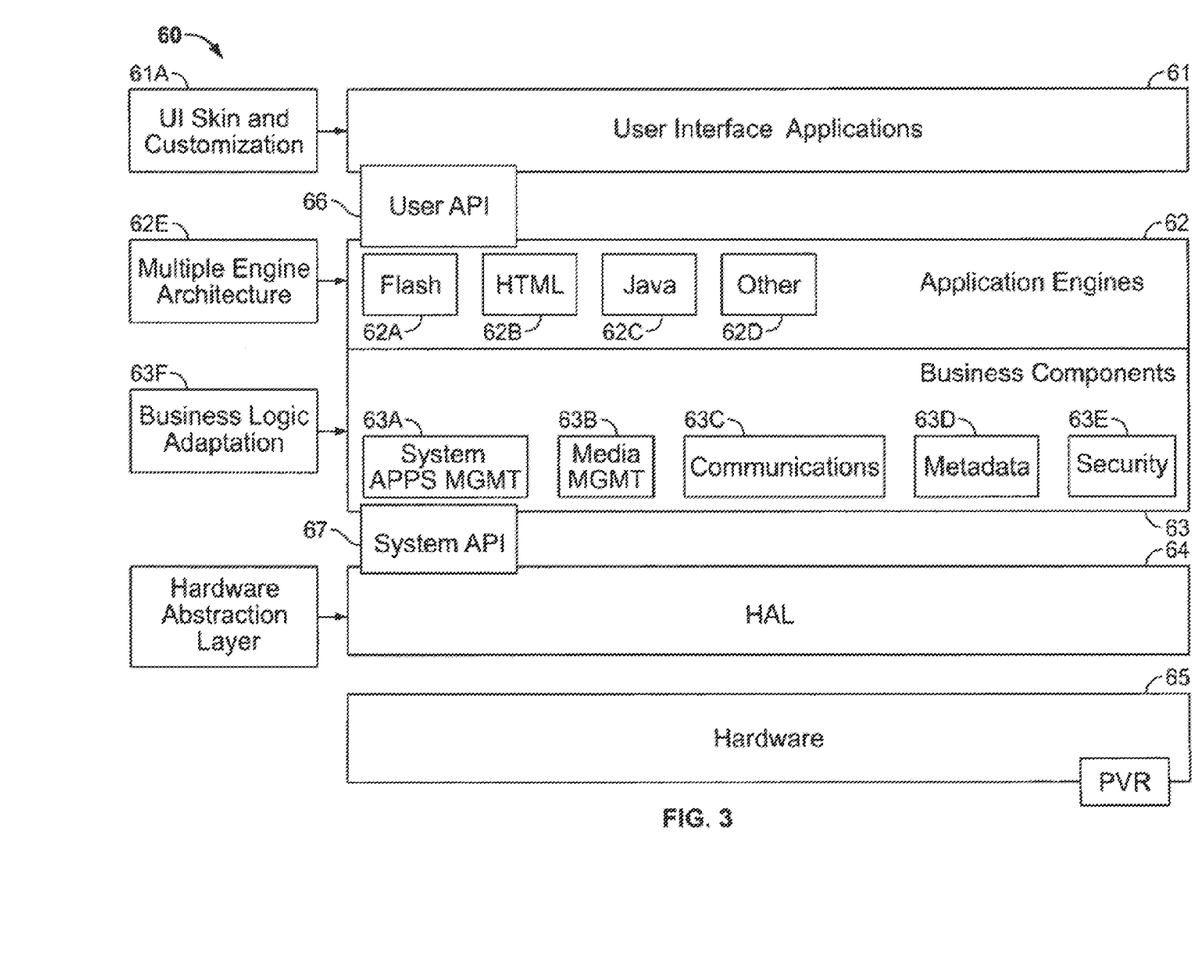
FIG. 3 is a schematic diagram of an exemplary embodiment of middleware.

As shown in FIG. 3, exemplary middleware 60 architecture may include components such as user interface applications 61, application engines 62, business components 63, a hardware abstraction layer 64, and hardware 65. The user interface applications 61 may include user interface skin and other customization 61A. A user application programming interface (API) 66 may link the user interface applications 61 with the application engines 62. The application engines 62 may include multiple engine architecture 62E, such as Flash 62A, HTML 62B, Java 62C, or other languages 62D. The business components 63 may include system and applications management 63A, media management 63B, communications 63C, metadata 63D, and security 63E and may incorporate business logic adaptation 63F. A system application programming interface (API) 67 may link the business components with the hardware abstraction layer 64.

Figure 4:
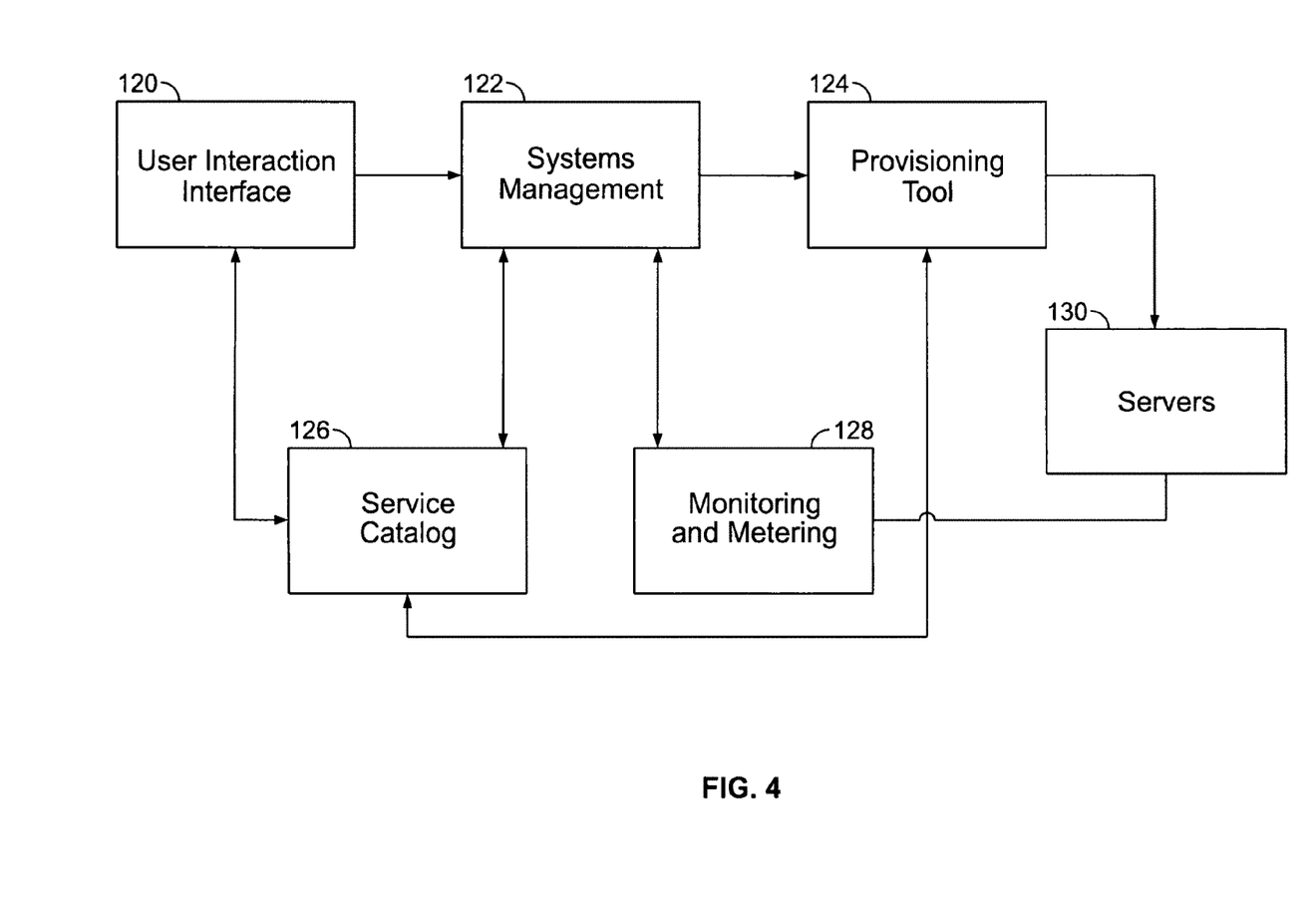
FIG. 4 is a schematic diagram of cloud computing architecture according to an exemplary embodiment.

As shown in FIG. 4, exemplary cloud computing architecture may include a user interaction interface 120, systems management component 122, a provisioning tool 124, a service catalog 126, monitoring and metering components 128, and servers 130, which may include one or more servers and/or one or more virtual servers. The user interaction interface may interact with the system management component 122 and the service catalog 126. The systems management component 122 may interact with the user interaction interface 120, the service catalog 126, the monitoring and metering components 128, and the provisioning tool 124. The provisioning tool 124 may interact with the system management component 122, the service catalog 126, and the servers 130. The servers 30 may interact with the provisioning tool 124 and the monitoring and metering components 128. The monitoring and metering components 128 may interact with the systems management component 122 and the servers 130. The service catalog 126 may interact with the user interaction interface 120, the systems management component 122, and the provisioning tool 124.

Exemplary embodiments of the disclosure may utilize encryption and/or other security features to maintain the security and integrity of the various data that is transferred within the system. For example, any or all of data 22, 24, queries 42, 44, and results 34, 26 may be encrypted prior to (and decrypted after) transfer between any of the components of the exemplary systems. Further, it is within the scope of the disclosure to utilize any known authentication system to verify the authority of the user 40 to query the system and/or receive results 26. For example, a user interface device may include a password-protected user interface. Further still, it is within the scope of the disclosure to store data within the cloud in an encrypted form.

As used herein, the term "real time" generally means as the data is being collected. It is to be understood that information incurring slight delays (such as data transmission time and minimal computer processing time) is considered to fall within this definition. More generally, as used herein, processes are conducted in real time so long as they are conducted substantially as the data is being collected. As used herein, the term "near real time" allows for further delays to the extent that it still appears to an end user that the processing is occurring substantially as the data is being collected. The speed may vary from application to application depending on the user's needs and expectations.

Some embodiments are pertinent to more medical uses than the exemplary applications discussed herein. In general, certain exemplary embodiments may be utilized whenever processing of data, such as medical data, may be advantageously performed by a cloud computing resource. For example, some embodiments may be useful where such processing includes performing calculations or analysis using collected data, modeling of collected data for interpretation, comparing of collected data with previously collected data or baseline data, or calculating of a risk factor based upon collected data.

Figure 6:
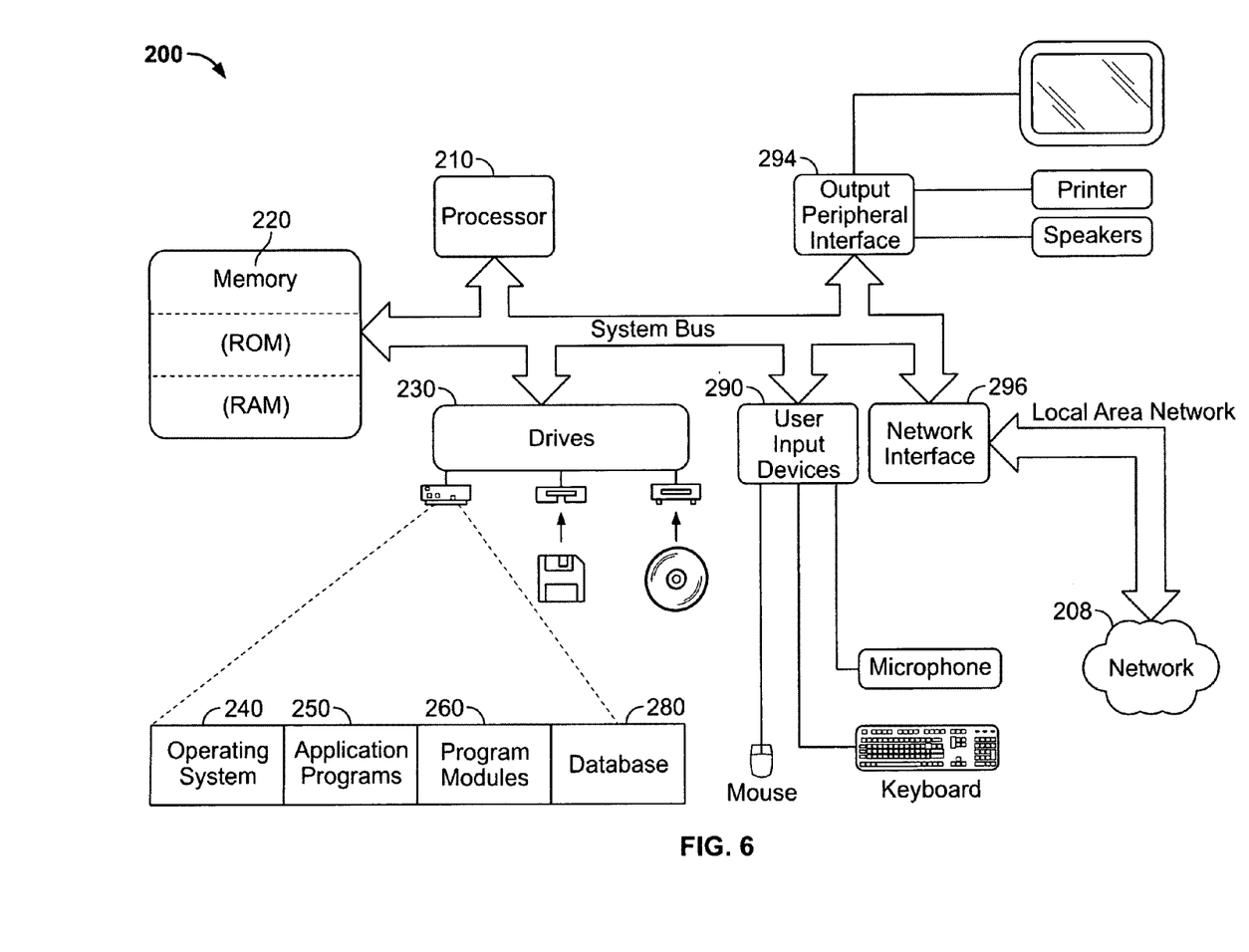
FIG. 6 is a schematic diagram of an exemplary computing system architecture for implementing embodiments.

With reference to FIG. 6, depicted is an exemplary computing system for implementing embodiments. FIG. 6 includes a computer 200, including a processor 210, memory 220 and one or more drives 230. The drives 230 and their associated computer storage media, provide storage of computer readable instructions, data structures, program modules and other data for the computer 200. Drives 230 can include an operating system 240, application programs 250, program modules 260, and database 280. Computer 200 further includes user input devices 290 through which a user may enter commands and data. Input devices may include an electronic digitizer, a microphone, a keyboard and pointing device, commonly referred to as a mouse, trackball or touch pad. Other input devices may include a joystick, game pad, satellite dish, scanner, or the like.

These and other input devices can be connected to processor 210 through a user input interface that is coupled to a system bus, but may be connected by other interface and bus structures, such as a parallel port, game port or a universal serial bus (USB). Computers such as computer 200 may also include other peripheral output devices such as speakers, which may be connected through an output peripheral interface 294 or the like.

Computer 200 may operate in a networked environment using logical connections to one or more computers, such as a remote computer connected to network interface 296. The remote computer may be a personal computer, a server, a router, a network PC, a peer device or other common network node, and can include many or all of the elements described above relative to computer 200. Networking environments are commonplace in offices, enterprise-wide area networks (WAN), local area networks (LAN), intranets and the Internet. For example, in the subject matter of the present application, computer 200 may comprise the source machine from which data is being migrated, and the remote computer may comprise the destination machine or vice versa. Note however, that source and destination machines need not be connected by a network 208 or any other means, but instead, data may be migrated via any media capable of being written by the source platform and read by the destination platform or platforms. When used in a LAN or WLAN networking environment, computer 200 is connected to the LAN through a network interface 296 or an adapter. When used in a WAN networking environment, computer 200 typically includes a modem or other means for establishing communications over the WAN, such as the Internet or network 208 It will be appreciated that other means of establishing a communications link between the computers may be used.

According to one embodiment, computer 200 is connected in a networking environment such that the processor 210 and/or program modules 260 can perform with or as a computing system for middleware communicating with a cloud computing resource in accordance with embodiments herein.

Figure 7:
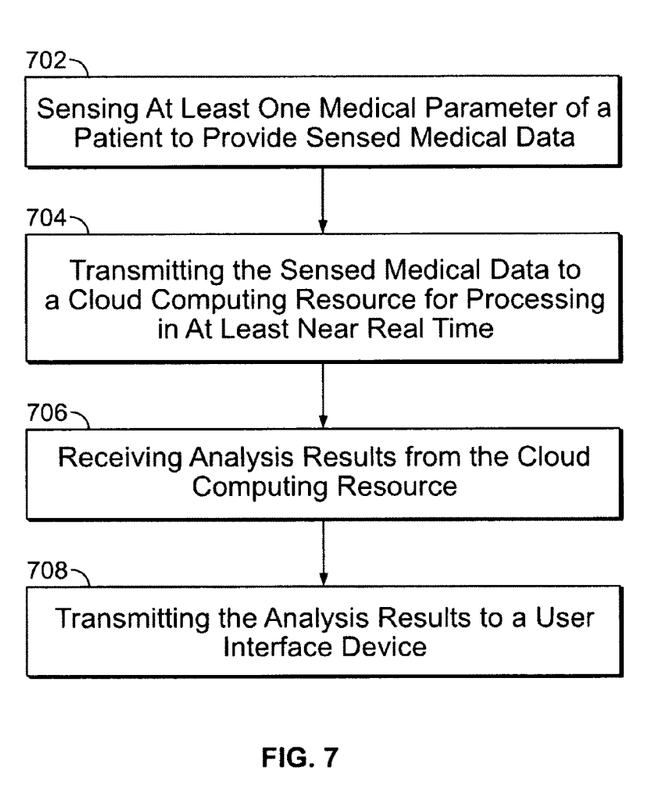
FIG. 7 is a flow chart depicting an exemplary embodiment.

In one exemplary embodiment (as shown in FIG. 7), a method of analyzing medical data may include sensing 702 at least one medical parameter of a patient to provide sensed medical data; transmitting 704 the sensed medical data to a cloud computing resource for processing in at least near real time; receiving 706 analysis results from the cloud computing resource; and transmitting 708 the analysis results to a user interface device.

Figure 8:
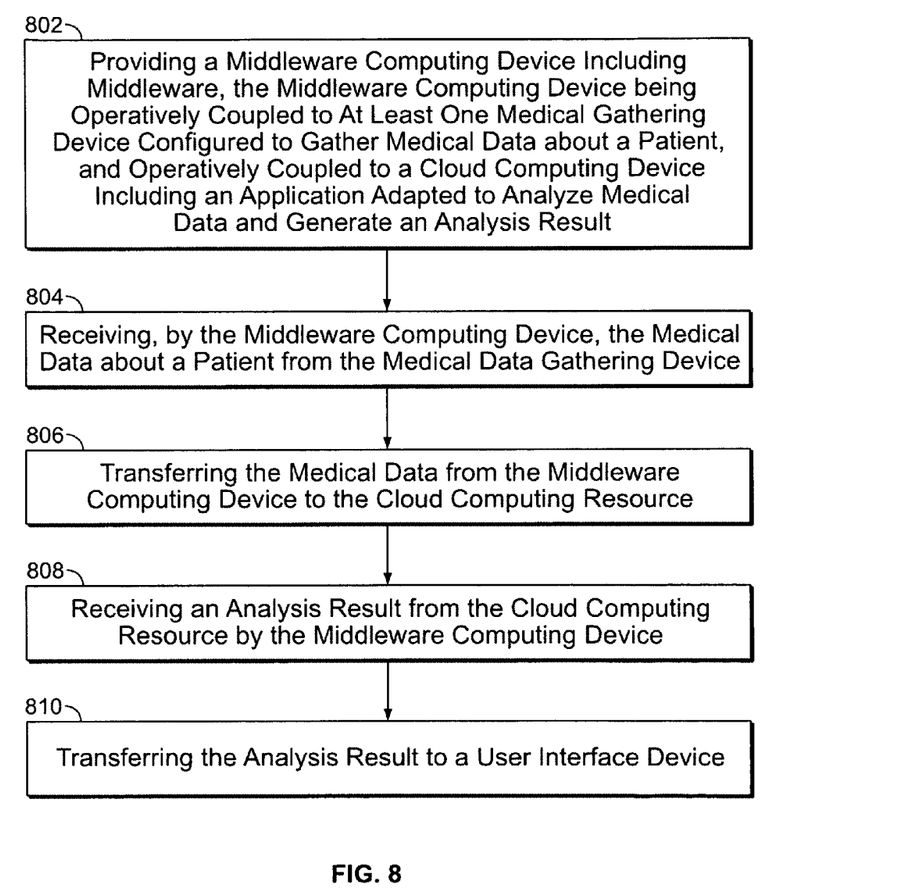
FIG. 8 is a flow chart depicting an exemplary embodiment.

In another exemplary embodiment (as shown in FIG. 8), a method of analyzing medical data may include providing 802 a middleware computing device including middleware, the middleware computing device being operatively coupled to at least one medical gathering device configured to gather medical data about a patient, and operatively coupled to a cloud computing device including an application adapted to analyze medical data and generate an analysis result; receiving 804, by the middleware computing device, the medical data about a patient from the medical data gathering device; transferring 806 the medical data from the middleware computing device to the cloud computing resource; receiving 808 an analysis result from the cloud computing resource by the middleware computing device; and transferring 810 the analysis result to a user interface device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of analyzing medical data, comprising:
sensing at least one medical parameter of a patient to provide sensed medical data;
transmitting the sensed medical data to a cloud computing resource via a middleware for processing in at least near real time, the middleware including an application engine, a user interface application linked to the application engine by a user programming interface, a business component operatively connected to the application engine, and a hardware abstraction layer linked to the business component by a system application programming interface, the hardware abstraction layer being situated between the application engine and the business component and a middleware hardware;
receiving analysis results from the cloud computing resource; and
transmitting the analysis results to a user interface device.

2. The method of claim 1, wherein sensing at least one medical parameter of a patient includes sensing a plurality of medical parameters.

3. The method of claim 2, wherein the plurality of medical parameters includes a plurality of vascular flow readings.

4. The method of claim 1, wherein sensing at least one medical parameter of a patient utilizes one or more topical sensors.

5. The method of claim 1, wherein sensing at least one medical parameter of a patient includes sensing electrocardiogram information.

6. The method of claim 1, wherein sensing at least one medical parameter of a patient includes sensing magnetic resonance information.

7. The method of claim 1, further comprising processing the sensed medical data with respect to at least one of demographic data, baseline medical data, prior medical data, and comparison medical data.

8. The method of claim 1, wherein the sensing at least one medical parameter of a patient, transmitting the sensed medical data to a cloud computing resource, receiving analysis results from the cloud computing resource, and transmitting the analysis results to a user interface device occur during a surgical procedure.

9. The method of claim 8, wherein the analysis results transmitted to the user interface device include a predictive warning.

10. The method of claim 8, wherein the surgical procedure is modified based upon the analysis results displayed by the user interface.

11. The method of claim 1, wherein the sensing at least one medical parameter of a patient, transmitting the sensed medical data to a cloud computing resource, receiving analysis results from the cloud computing resource, and transmitting the analysis results to a user interface device occur in real time.

12. The method of claim 1, wherein transmitting the sensed medical data to a cloud computing resource, receiving the analysis results from the cloud computing resource, and transmitting the analysis results to the user interface device are performed by the middleware.

13. The method of claim 1, wherein sensing at least one medical parameter of a patient includes sensing a plurality of medical parameters of the patient utilizing directional microphones.

14. The method of claim 1, wherein sensing at least one medical parameter of a patient includes sensing a plurality of medical parameters of the patient utilizing arterial wall sensors.

15. The method of claim 14, wherein sensing at least one medical parameter of a patient includes sensing a plurality of medical parameters of the patient utilizing arterial wall sensors in tandem with blood volumetric flow rate sensors.

16. The method of claim 1, wherein sensing at least one medical parameter of a patient includes sensing a plurality of medical parameters, including blood flow and arterial wall thickness parameters.

17. The method of claim 16, further comprising processing the sensed medical data with respect to at least one of demographic data, baseline medical data, prior medical data, and medical data.

18. A method of analyzing medical data, comprising:
providing a middleware computing device including middleware, the middleware computing device being operatively coupled to at least one medical gathering device configured to gather medical data about a patient, and operatively coupled to a cloud computing resource including an application adapted to analyze medical data and generate an analysis result, the middleware computing device providing an application engine, a user interface application linked to the application engine by a user programming interface, a business component operatively connected to the application engine, and a hardware abstraction layer linked to the business component by a system application programming interface, the hardware abstraction layer being situated between the application engine and the business component and a middleware hardware;
receiving, by the middleware computing device, the medical data about a patient from the medical data gathering device;
transferring the medical data from the middleware computing device to the cloud computing resource;
receiving an analysis result from the cloud computing resource by the middleware computing device; and
transferring the analysis result to a user interface device.

19. The method of claim 18, wherein receiving, by the middleware computing device, the medical data from the medical data gathering device is performed substantially as the medical data is being gathered.

20. The method of claim 18, wherein transferring the analysis result to a user interface device is performed substantially as the medical data is being gathered.

21. The method of claim 18, wherein the user interface device is located proximate the medical data gathering device.

22. The method of claim 18, further comprising, before transferring the analysis result to the user interface device, formatting the analysis result, by the middleware, for display on the display device.

23. The method of claim 18, wherein the medical data includes vascular system data.

24. The method of claim 18, wherein the medical data includes electrocardiogram data.

25. The method of claim 18, wherein the medical data includes blood flow data.

26. The method of claim 18, wherein the medical data includes imaging data.

27. The method of claim 26, wherein the imaging data includes magnetic resonance imaging data.

28. The method of claim 18, further comprising comparing the medical data with baseline medical data.

29. The method of claim 28, wherein comparing the medical data includes comparing the medical data with previously obtained medical data from the same patient.

30. The method of claim 28, wherein comparing the medical data includes comparing the medical data with previously obtained medical data from at least one other patient.

31. The method of claim 18, wherein the medical data includes demographic data about the patient; and the method further comprising considering the patient's demographic data.

32. The method of claim 18, wherein transferring the analysis result to a user interface device is performed during a testing procedure and the method further includes adjusting the testing procedure based upon the analysis result.

33. The method of claim 18, wherein transferring the analysis result to a user interface device is performed during a surgical procedure and the method further includes adjusting the surgical procedure based upon the analysis result.

34. The method of claim 18, further comprising, before transferring the analysis result to the user interface device, querying a user for a password.

35. A medical data processing system comprising:
a middleware computing device including middleware, the middleware computing device adapted to receive sensed medical data from a medical data sensing device, and the middleware computing device being operatively coupled to a cloud computing resource having at least one application for processing the sensed medial data and being operatively coupled to a user interface device, the middleware computing device including an application engine, a user interface application linked to the application engine by a user programming interface, a business component operatively connected to the application engine, and a hardware abstraction layer linked to the business component by a system application programming interface, the hardware abstraction layer being situated between the application engine and the business component and a middleware hardware.

36. The medical data processing system of claim 35, further comprising the medical data sensing device and the user interface device, wherein the medical data sensing device and the user interface device are collocated proximate a patient.

37. The medical data processing system of claim 35, further comprising the medical data sensing device and the user interface device, wherein the medical data sensing device and the user interface device are portable and are operatively connectable to the middleware computing device from a plurality of locations.

38. The medical data processing system of claim 35, further comprising the medical data sensing device, wherein the medical data sensing device includes at least one sensor adapted to sense at least one parameter relating to a patient's body.

39. The medical data processing system of claim 38, wherein the medical data sensor device includes at least one of the following:
at least one sensor for performing vascular testing;
an electrocardiogram electrode;
a topical sensor;
at least one blood flow sensor; and
a magnetic resonance data receptor.

40. The medical data processing system of claim 38, wherein:
the medical data sensing device includes a plurality of sensor inputs and is configured to communicate the sensed medical data from the plurality of sensor inputs in at least near real time to the middleware computing device;
the middleware computing device is configured to route the sensed medical data to the cloud computing resource in at least near real time; and
the cloud computing resource is configured to process the sensed medical data in at least near real time.

41. The medical data processing system of claim 39, wherein the middleware computing device is further configured to condition a data result received from the cloud computing resource for viewing on the user interface device.

42. The medical data processing system of claim 40, wherein:
the cloud computing resource has access to at least one of demographic data, baseline medical data, prior medical data, and comparison medical data; and
the cloud computing resource is configured to process the sensed medical data with respect to the at least one of demographic data, baseline medical data, prior medical data, and comparison medical data.

43. The medical data processing system of claim 40, wherein the middleware computing device is configured to condition the sensed medical data that is routed to the cloud computing resource.

44. The medical data processing system of claim 35, wherein the cloud computing resource includes one or more servers.

45. The medical data processing system of claim 44, wherein the one or more servers includes at least one virtual server.

46. The medical data processing system of claim 35, further comprising the medical data sensing device and the user interface device, wherein the medical data sensing device includes a plurality of medical data sensing devices and the user interface device includes a plurality of user interface devices, and wherein each of the medical data sensing devices and each of the user interface devices is operatively connected to the middleware computing device.

* * * * *

UNITED STATES PATENT AND TRADEMARK OFFICE
CERTIFICATE OF CORRECTION

PATENT NO.      : 9,095,274 B2
APPLICATION NO. : 12/202282
DATED           : August 4, 2015
INVENTOR(S)     : Fein et al.

It is certified that error appears in the above-identified patent and that said Letters Patent is hereby corrected as shown below:

In the Specification

In Column 1, Line 7, delete "system's" and insert -- systems --, therefor.

In Column 1, Line 19, delete "procedure's," and insert -- procedures, --, therefor.

In Column 4, Line 8, delete "ultra sound" and insert -- ultrasound --, therefor.

In Column 5, Line 31, delete "may bee" and insert -- may be --, therefor.

In Column 8, Line 16, delete "paramount" and insert -- paramount, --, therefor.

Signed and Sealed this
Twenty-first Day of June, 2016

Michelle K. Lee
*Director of the United States Patent and Trademark Office*